United States Patent [19]

Heimburger et al.

[11] 4,056,484
[45] Nov. 1, 1977

[54] STABLE BLOOD PLASMA, PROCESS FOR PREPARING IT AND ITS USE AS COMPARATIVE PLASMA IN COAGULATION TESTS

[75] Inventors: Norbert Heimburger; Axel Sieber, both of Marburg, Lahn; Horst Schwinn, Marburg-Michelbach, all of Germany

[73] Assignee: Behringwerke Aktiengesellschaft, Marburg, Lahn, Germany

[21] Appl. No.: 644,519

[22] Filed: Dec. 29, 1975

[30] Foreign Application Priority Data

Dec. 31, 1974 Germany .............................. 2461969

[51] Int. Cl.² ........................................... G01N 33/16
[52] U.S. Cl. ................................. 252/408; 23/230 B; 424/101

[58] Field of Search .................... 252/408, 299; 62/60; 23/230 B; 424/2, 11, 101; 195/103.5 C

[56] References Cited

U.S. PATENT DOCUMENTS

| | | | |
|---|---|---|---|
| 3,466,249 | 9/1969 | Anderson | 252/408 |
| 3,629,142 | 12/1971 | Marbach | 252/408 |
| 3,682,835 | 8/1972 | Louderback | 252/408 |
| 3,876,375 | 4/1975 | Maurukas | 252/408 |
| 3,897,363 | 7/1975 | Louderbeck et al. | 252/408 |

*Primary Examiner*—Benjamin R. Padgett
*Assistant Examiner*—Irwin Gluck
*Attorney, Agent, or Firm*—Curtis, Morris & Safford

[57] ABSTRACT

Lyophilized blood plasma under a protective gas wherein the protective gas contains at least 5% of carbon dioxide.

4 Claims, No Drawings

STABLE BLOOD PLASMA, PROCESS FOR PREPARING IT AND ITS USE AS COMPARATIVE PLASMA IN COAGULATION TESTS

The invention relates to a blood plasma which with regard to its coagulation properties in test systems suitable for coagulation examinations shows a relatively unchanged behavior and is, therefore, suitable as standard plasma for coagulation tests; the invention further relates to a process for preparing the blood plasma and its use especially for diagnostic coagulation examinations.

A peculiar property of the blood outside the vessels is its coagulation. It appears, however, that the coagulation times of patients having determined diseases differ from those of healthy normal persons. These differences may also be brought about by certain pharmaceutical products. It is also known that the blood coagulation results from the concurrence of various activating and inhibiting factors. The coagulation factors are more or less sensitive and their storage without any loss of activity implies great difficulties. It especially appears that stored blood plasmas are very soon subject to changes as to their coagulation parameters. In the diagnostic control of the state of coagulation it is necessary to correlate the values obtained in the individual blood coagulation tests to certain normal values.

A suitable reference system is for example a mixed plasma of several healthy blood donors which should be obtained simultaneously with the plasma of the person being tested. Such procedure cannot always be carried out in diagnostic laboratories.

Therefore, the object of the present invention is to prepare a blood plasma capable of being stored which has a good stability as to the factors important for the state of coagulation. Important coagulation parameters are the single-phase cogulation time according to Quick, the partial thromboplastin time, the plasmathrombin time, the coagulation factors II, V, X and XIII and finally fibrinogen.

It is known that as to the coagulation properties, freshly obtained plasma of healthy donors sufficiently fulfils the criteria for a reference system in coagulation examinations. It is also known that a plasma may also be stabilized by lyophilization with regard to the activity of the coagulation factors. But it has also appeared that the coagulation parameters of the lyophilized plasmas change in course of time in different manners. The result is that lyophilized plasmas which may be taken as a standard in coagulation examinations, cannot be used for all of the above-mentioned coagulation parameters. It has turned out that the plasmathrombin coagulation time of the redissolved lyophilized plasmas does not agree with the values to be obtained by normal plasma, already at the moment when the other coagulation factors are relatively well in line with normal values.

It has now been found surprisingly that a lyophilized blood plasma which is stored under a protective gas remains stable at least with regard to the following coagulation parameters if the protective gas contains at least 5%, preferably 10–50 % of carbon dioxide. The coagulation parameters concerned are especially Quick time, partial thromboplastin time, plasmathrombin coagulation time, the coagulation factors II (prothrombin), V (accelerin), X (Stuart-Prower-factor), XIII (fibrin-stabilizing factor) and fibrinogen.

The invention therefore relates to a lyophilized blood plasma under a protective gas wherein the protective gas contains at least 5%, preferably 10–50% of carbon dioxide. Further constituents which may be contained in the protective gas beside carbon dioxide are the gases well-known for this purpose. Those are generally inert substances present in a gaseous phase at $-25°$ C. To these gases belong above all nitrogen, but also other inert gases, for example the noble gases such as helium, neon or argon. As is generally necessary for blood plasmas the plasma contains an anticoagulating agent added to avoid blood coagulation, for example oxalate or citrate ions in a concentration usual in the obtention of plasma of about 1 part of anti-coagulating agent and 9 parts of blood and, if desired, further colloid-stabilizing additives, preferably in the form of low-molecular weight hydrocarbons, these in a concentration of 1 to 5%.

The invention further relates to a process for preparing stabilized blood plasma, wherein lyophilized, if desired stabilized, blood plasma is introduced into a protective gas containing carbon dioxide in the concentration indicated. The invention especially concerns a process according to which vessels containing lyophilized blood plasma are evacuated and the vacuum is filled with a protective gas containing carbon dioxide in the amount mentioned.

In a preferred variant, freshly obtained blood is added in known manner to an amount of an anticoagulating agent; when using citrate, for example 1 part by volume of a 0.1 molar sodium citrate solution of pH 7.0 is mixed with 9 parts by volume of the freshly obtained blood. The blood is centrifuged, for example at 7,500 $\pm$ 500 g for 20 to 40 minutes, preferably for 30 minutes and the plasma over the blood corpuscles is decanted and, if desired, mixed with stabilizing substances. The plasma is then filled into glass vessels having an unwettable surface, which are preferably siliconized, or into corresponding plastic vessels; care has to be taken that the amount of plasma filled in only takes one-third to one-tenth of the total volume of the vessel. The plasma is frozen in the vessels with a surface as large as possible — which may preferably be obtained by rotating freezing — and finally dried. The vessels containing the dried plasma are evacuated and it has proved advantageous to create a vacuum of $10^{-3}$ to $10^{-4}$ mm mercury and to leave the plasmas for 2 to 5 hours, preferably 3 to 4 hours, in the vacuum, then to fill this vacuum with a protective gas containing carbon dioxide and to close the vessels hermetically.

It is known that the coagulation mecanism is, in principle, similar for all vertebrates, so that there is no reason why according to the purpose desired each blood plasma of vertebrates shall not be stabilized in the form described with regard to the coagulation parameter. But in clinical diagnosis there is a need for human plasmas with standardized coagulation parameters so that the starting material for the lyophilized plasma of the invention is preferably human blood plasma. Especially blood plasmas obtained from healthy donors are mixed and stabilized according to the invention. But nevertheless plasmas of persons to be tested having determined coagulation disturbances may be worked up in the same way to be ready for use as a stable reference system for the determination or identification of a corresponding coagulation disturbance.

Stabilizing substances have hitherto been added to the blood plasmas or sera, especially for the stabilization of the blood plasma proteins, preferably in the form of low-molecular weight hydrocarbons.

In the scope of the present invention it has also proved advantageous to add such compounds. But care has to be taken that the substances used do not influence the coagulation system. From this point of view the stabilizing substances to be added to the lyophilizing plasmas are preferably neutral carbohydrates in a concentration of up to 5 % by weight. Particularly suitable are, for example lactose saccharose and lactose which may be present in the plasma individually or together at 1–2 %. It has also proved advantageous to add to the plasma buffer substances capable of adjusting the liquid plasma to a pH of from about 7.1 to 7.2; in this case, too, care must be taken that buffer substances are chosen which in the amount required do not influence the coagulation system in the present plasma, do not form any complex and have $pK_1$-values of about 6 to 8.5. Among the buffer substances proposed in this respect by N.E. Good et al. 1966 (*Biochemistry* 5, 467,477) which have to a large extent an inert behavior in biochemical systems, N-2-hydroxy-ethyl-piperazino-N-ethane-sulfonic acid (Hepes) buffer in a concentration of up to 0.01 mol has proved favorable. The difficulty which arises with buffer additives is, for example, that the addition of a buffer in solid form causes a local displacement of the pH value in the plasma with the consequence that the coagulation system is disturbed, whereas the addition of the buffer is dissolved form brings about an inadmissible dilution of the plasma.

The blood plasma stored under a protective gas containing carbon dioxide is used, due to its stability, as a comparative plasma in coagulation examinations, especially to determine the Quick value of the partial thromboplastin time, the plasma-thrombin coagulation time, the coagulation factors II, V, X, XIII and of the fibrinogen. The methods of determination are effected for example according to the following processes:

1. Quick Value

1 Part of a sodium citrate solution of 0.1 mol per liter and a pH value of 4.5 to 7 is carefully mixed with 9 parts of venous blood of the person to be tested, the formation of foam being avoided, and centrifuged for 10 minutes at about 3,000 rpm corresponding to 1,500 x g. The supernatent plasma is decanted and stored at 4° C until the test is carried out. 0.2 ml of a calcium thromboplastin solution also pre-heated to 37° C is added to 0.1 ml of plasma also pre-heated to 37° C and observed with the aid of known processes to determine the time until coagulation takes place, for example according to the hook method, ball method, tipping method or with automatic coagulometers.

The coagulation time found is correlated to a previously drawn standard curve while using the blood plasma stored according to the invention or freshly obtained. The norm of the Quick value for normal plasmas which have been freshly obtained or stored according to the invention is 12 to 16 seconds for undiluted plasma.

The determination of the Quick value is a test for finding out insufficiencies of the factors VII, X, V, II and I taking part in the exogenic coagulation system.

2. Partial Thromboplastin Time

For the determination of the partial thromboplastin time, the plasma is obtained in the same manner as described for the Quick time, and equal parts (0.2 ml) of the plasma and 0.2 ml of a suspension of washed human thrombocytes with an addition of kaolin are incubated for 2 minutes at 37° C. To 0.2 ml of the incubation mixture, a 0.025 molar calcium chloride solution is added and the time until coagulation takes place is measured in the manner described for the Quick time. The partial thromboplastin time shows normal values between 40 and 60 seconds. Coagulation times exceeding 55 seconds indicate coagulation disturbances and require detailed examinations especially of the factors VIII and IX.

3. Plasma Thrombin Coagulation Time

For the determination of the plasma thrombin coagulation time citrated plasma — as described for the Quick time — is incubated with the same volume of a solution containing 6 units of thrombin per ml, and the coagulation time is determined in known manner. The normal values for the plasmathrombin coagulation time are between 17 and 24 seconds. The plasma thrombin coagulation time serves above all for the observation of a streptokinase or heparin therapy. In a streptokinase therapy, coagulation times in this test system of from 34 to 96 seconds are found, whereas a heparin therapy extends the coagulation time to from 34 to 110 seconds.

4. Coagulation Factors II and V

The determination of the coagulatin factors II and V may take place simultaneously. For this purpose the plasma to be tested is obtained in the same manner as described for the Quick value and the plasma is incubated with the same volume (0.1 ml) of a factor-II- or factor-V-insufficient plasma. As described for the determination of the Quick value, 0.2 ml of a calcium thromboplastin solution is added in each case to both mixtures and the coagulation time is subsequently determined in known manner. The measured coagulation time is proportional to the concentrations of the coagulation factors II and V. The content of the coagulation factors is read off from a standard curve which has been drawn with fresh normal plasma or with normal plasma that has been stored according to the invention. The determination of the concentration of the coagulation factor II serves for the detailed detection of prothrombin insufficiencies, whereas that of the factor V is indicated when there is a suspicion of parahemophilia.

5. Coagulation Factor X

The determination of the coagulation factor X also takes place with the citrated plasma which is also used for the determination of the Quick time. The plasma is incubated in a dilution of 1:20 with the same volumes (0.1 ml) of a factor-X-insufficient plasma and of a solution of snake-poison thromboplastin for 30 seconds at 37° C, then 0.1 ml of a 0.025 molar calcium chloride solution is added and the coagulation time is determined in known manner. The resulting coagulation time is proportional to the factor X concentration of the plasma to be tested. The factor X content is read off from a standard curve which has been drawn with the aid of a freshly obtained mixed plasma of normal persons or of a plasma stored according to the invention.

6. Coagulation Factor XIII

In the determination of the factor XIII, the obtention of the citrated plasma takes place in the presence of a polyvalent proteinase inhibitor of 2.5 antiplasmin units per ml of blood. Carrying out the determination requies an antifactor-XIII-serum which is incubated in a series of dilutions with plasma for 30 minutes at room temperature. Then antiserum with plasma, thrombin and calcium chloride are added to each incubation mixture, which brings the plasma to coagulation. To form a complete coagulum the batches are allowed to stand for about one hour at room temperature. By addition of a 1% monochloroacetic acid solution to each incubation mixture, the plasma dilution is determined in such a degree that the coagulum has just dissolved in the monochloro-acetic acid. The amount of the factor XIII in the plasma to be determined is correlated to the amount which results from the determination of the factor XIII in normal plasmas which may be freshly obtained or stored according to the invention.

7. Fibrinogen

The determination of fibrinogen is also effected with citrated plasma which is brought to coagulation with thrombin. The coagulum formed is obtained by centrifugation at 45,000 rpm as a sediment. The supernatant is decanted, the sediment washed several times with an isotonic sodium chloride solution and finally dried in vacuo. Via a determination of the nitrogen content according to Kjeldahl, the protein content of the coagulum is calculated in mg; it is indicated as fibrinogen. In this case too, the content of fibrinogen of the normal plasma stored according to the invention serves as a reference system.

The following Example illustrates the invention.

EXAMPLE

To 50 ml of a citrate buffer solution having a content of 0.1 mol/l of sodium citrate and a pH value of 7.0 which is sterile and free from stabilizers, 450 ml of venous blood of a healthy doner were cautiously added while avoiding the formation of foam, and both components were mixed carefully. The citrated blood was centrifuged at 8,000 g for 30 minutes and the plasma was siphoned off. The plasma was mixed with the citrated plasma, obtained in the same manner, of 9 further donors so that a pool of 10 healthy blood donors resulted on the whole. Lactose and saccharose were added to the plasma mixture in each case up to a final concentration of 1%. Furthermore, with an addition of 4 g of N-2-hydroxy-ethyl-piperazino-N-ethane-sulfonic acid (HEPES) per liter of plasma, the pH value of the plasma was adjusted to 7.1. The plasma mixture was then filled by 1.0 ml portions into vessels having a total content of 6.5 ml and frozen as a block. The frozen plasma was dried in a lyophilization plant. Then a vacuum of $5 \times 10^{-4}$ was produced. The lyophilized plasmas were left for 3 hours in this vacuum. Then carbon dioxide gas was introduced into the vacuum until balance with the atmospheric pressure was established. Then the vessels were closed hermetically.

A quality test of 5 samples chosen ad libitum yielded on an average for the Quick time, the partial thromboplastin time was 41.8 seconds, and the plasmathrombin coagulation time was 19.4 seconds. It has appeared that these values after some months' storage even at 37° C were nearly unchanged and that on storage at 4° C over more than 3 years only insignificant changes are to be expected.

Instead of carbon dioxide a mixture of 50% of carbon dioxide and 50% of nitrogen (v:v) or a mixture of 5% of carbon dioxide and 95% of nitrogen may be filled into the vacuum; for example the nitrogen may be replaced by a mixture of an inert stable noble gas, such as helium, neon or argon, with the carbon dioxide.

What we claim is:

1. Lyophilized blood plasma containing an anticoagulating agent and present in a sealed container under a protective gas containing at least 5 percent of carbon dioxide.

2. Lyophilized blood plasma as in claim 1 which additionally contains a colloid-stabilizing additive.

3. A method for making lyophilized blood plasma as in claim 1, which method comprises mixing fresh blood with an anticoagulating agent, centrifuging said mixture and separating the plasma component thereof, filling said plasma into a non-wettable container, freezing said plasma to form frozen plasma having a large surface area, lyophilizing said frozen plasma, evacuating said container, introducing said protective gas into said container, and then sealing said container.

4. In a method for determining a component of blood plasma by observing the coagulation behavior of a plasma sample to be tested and comparing this behavior with the coagulation behavior of a plasma of known characteristics, the improvement wherein said plasma of known characteristics is prepared from lyophilized blood plasma as in claim 1.

* * * * *